United States Patent
Cho

(10) Patent No.: US 8,967,853 B2
(45) Date of Patent: Mar. 3, 2015

(54) METHOD AND APPARATUS FOR MIXING FLUIDS

(75) Inventor: Seung-Hei Cho, Yongin-si (KR)

(73) Assignee: Samsung Electronics Co., Ltd., Suwon-Si, Gyeonggi-Do (KR)

( * ) Notice: Subject to any disclaimer, the term of this patent is extended or adjusted under 35 U.S.C. 154(b) by 1114 days.

(21) Appl. No.: 12/496,372

(22) Filed: Jul. 1, 2009

(65) Prior Publication Data

US 2010/0002535 A1    Jan. 7, 2010

(30) Foreign Application Priority Data

Jul. 3, 2008    (KR) ........................ 10-2008-0064346

(51) Int. Cl.
*B01F 5/06*    (2006.01)
*B01F 13/00*    (2006.01)
*B01F 13/02*    (2006.01)
(Continued)

(52) U.S. Cl.
CPC ............ *B01F 5/0682* (2013.01); *B01F 5/0688* (2013.01); *B01F 13/0059* (2013.01); *B01F 13/0222* (2013.01); *B01F 13/0227* (2013.01); *B01J 19/0093* (2013.01); *B01L 3/502753* (2013.01); *B01J 2219/00788* (2013.01); *B01J 2219/00889* (2013.01); *B01J 2219/00909* (2013.01); *B01J 2219/0277* (2013.01); *B01J 2219/0281* (2013.01); *B01J 2219/0295* (2013.01); *B01L 2300/0681* (2013.01); *G01N 2035/00544* (2013.01)
USPC .................. 366/176.1; 366/181.6; 366/177.1; 366/340

(58) Field of Classification Search
USPC ............ 366/336–340, 176.1, 177.1, 181.5, 6
See application file for complete search history.

(56) References Cited

U.S. PATENT DOCUMENTS 6,086,243 A    7/2000    Paul et al.
6,287,850 B1   9/2001    Besemer et al.
(Continued)

FOREIGN PATENT DOCUMENTS

JP    2005-308731    11/2005
JP    2008-114099    5/2008
(Continued)

OTHER PUBLICATIONS

Korean Patent abstracts: English Abstract for Publication No. 1020030028306 (for 10-0413536), Application Publication date: Apr. 8, 2003, 10 pgs.
(Continued)

*Primary Examiner* — Tony G Soohoo
(74) *Attorney, Agent, or Firm* — F. Chau & Associates, LLC

(57) ABSTRACT

Provided are a method and apparatus for mixing fluids, whereby small amounts of fluids are effectively mixed. An apparatus for mixing fluids includes: a chamber comprising a first region and a second region; a fluid influx channel connected to the first region through which a plurality of fluids flow into the chamber; a turbulent flow generation film interposed between the first region and the second region that includes through-holes through which the fluids are passed to generate turbulent flow in the fluids in the second region to mix the fluids; and a first fluid discharge channel connected to the second region through which the mixed fluids are discharged. Fluids are mixed without additional external devices. Thus, an apparatus for mixing fluids may be miniaturized while effectively mixing fluids.

11 Claims, 11 Drawing Sheets

(51) Int. Cl.
*B01J 19/00* (2006.01)
*B01L 3/00* (2006.01)
*G01N 35/00* (2006.01)

(56) References Cited

U.S. PATENT DOCUMENTS

| | | | |
|---|---|---|---|
| 6,350,016 B1* | 2/2002 | Tachihara et al. | 347/56 |
| 6,551,817 B2 | 4/2003 | Besemer et al. | |
| 6,790,651 B2 | 9/2004 | Tanaka et al. | |
| 6,932,502 B2* | 8/2005 | Childers et al. | 366/152.1 |
| 6,935,772 B2 | 8/2005 | Karp et al. | |
| 7,294,310 B2* | 11/2007 | Yamazaki et al. | 422/514 |
| 8,066,918 B2* | 11/2011 | Noritomi et al. | 264/4.1 |
| 2002/0086136 A1* | 7/2002 | Ahn et al. | 428/137 |
| 2004/0258569 A1* | 12/2004 | Yamazaki et al. | 422/100 |
| 2005/0084866 A1 | 4/2005 | Caren et al. | |
| 2005/0142664 A1 | 6/2005 | Loney | |
| 2005/0221281 A1 | 10/2005 | Ho | |
| 2005/0252772 A1 | 11/2005 | Paul et al. | |
| 2005/0270895 A1* | 12/2005 | Strang | 366/107 |
| 2007/0047388 A1 | 3/2007 | DeNatale et al. | |
| 2007/0140041 A1 | 6/2007 | Sparey-Taylor et al. | |
| 2007/0222812 A1* | 9/2007 | Tokuno et al. | 347/22 |
| 2007/0228588 A1* | 10/2007 | Noritomi et al. | 264/4.1 |

FOREIGN PATENT DOCUMENTS

| | | |
|---|---|---|
| KR | 10-0413536 | 12/2003 |
| KR | 10-0472058 | 2/2005 |
| KR | 10-0509254 | 8/2005 |
| KR | 10-0563840 | 3/2006 |
| KR | 10-0635110 | 10/2006 |
| WO | WO2004036041 | 4/2004 |

OTHER PUBLICATIONS

Korean Patent abstracts: English Abstract for Publication No. 1020040039571 (for 10-0472058), Application Publication date: May 12, 2004, 14 pgs.
Korean Patent abstracts: English Abstract for Publication No. 1020040100245 (for 10-0509254), Application Publication date: Dec. 2, 2004, 21 pgs.
Korean Patent abstracts: English Abstract for Publication No. 1020050010423 (for 10-0563840), Application Publication date: Jan. 27, 2005, 14 pgs.
Patent abstracts of Japan English Abstract for Publication No. 2005-308731, Application Publication date: Nov. 4, 2005, 24 pgs.
Korean Patent abstracts : English Abstract for Publication No. 1020060064807 (for 10-0635110), Application Publication date: Jun. 14, 2006, 18 pgs.
Korean Office Action Dated Nov. 7, 2014.
Korean Office Action Dated Nov. 7 2014 (English Translation).

* cited by examiner

METHOD AND APPARATUS FOR MIXING FLUIDS

CROSS-REFERENCE TO RELATED APPLICATIONS

This application claims the benefit of Korean Patent Application No. 10-2008-0064346, filed on Jul. 3, 2008, in the Korean Intellectual Property Office, the contents of which are herein incorporated by reference in their entirety.

BACKGROUND

1. Technical Field

Embodiments of the present invention are directed to a method and apparatus for mixing fluids, whereby the fluids are mixed due to the generation of turbulent flow.

2. Description of the Related Art

Biochips and biosensors are micro devices that allow various experiments and assays currently performed in a laboratory to be performed on a single small chip. Examples of biochips include microfluidic chips that are commonly used for gene assays or biochemical assays. With regard to microfluidic chips, a small amount of a sample is loaded into micro channels formed in a microfluidic chip so as to react with various chemical molecular sensors integrated in the microfluidic chip. Microfluidic chips are designed to perform isolation, synthesis, and quantification of a sample. Assays using biochips use effective mixing operations of various samples, such as operations for cell activation, enzyme reactions, and protein synthesis. However, in a micro-level system, fluids have a small Reynolds number and thus flow in a laminar flow pattern, and samples in microfluidic devices are mixed only by diffusion. Thus, a long time is required to effectively mix samples, thereby affecting the entire assay system.

Conventional techniques for effectively mixing micro samples can be classified into active mixing methods and passive mixing methods. Active fluid mixers used in active mixing methods use external energy, such as external pressure or an electric field, and actively control fluid flow. For example, magnetic beads or pneumatic devices may be used. However, when magnetic beads are used, additional devices for moving the magnetic beads, as well as additional processes of loading the magnetic beads into a chamber, are required, thus complicating the manufacturing process. When pneumatic devices are used, many switches need to be formed in the channels, which also complicates the manufacturing process.

On the other hand, passive mixing methods do not use additional energy but only use fluids flowing at a predetermined flow rate, and mixing performance is improved only by changing the structure of the channels. Although passive mixing methods have lower mixing performance than active mixing methods, passive mixing methods are inexpensive and useful for micro devices. For example, structures for passive mixing methods include stacked films having T-shaped or Y-shaped fluidic structures, or slanted recesses arranged in channels. However, these structures are complex and challenging to manufacture, and effective mixing does not occur.

SUMMARY OF THE INVENTION

One or more embodiments of the invention include a method and apparatus for effectively mixing micro fluids.

Additional aspects will be set forth in part in the description which follows and, in part, will be apparent from the description, or may be learned by practice of the presented embodiments.

According to one or more embodiments of the present invention, a method of mixing fluids includes: loading a plurality of fluids into a first region of a chamber through a fluid influx channel; passing the loaded fluids into a second region of the chamber through through-holes of a turbulent flow generation film, thereby forming bubbles; mixing the fluids in the second region of the chamber by turbulent flow generated when the bubbles burst or are separated from the turbulent flow generation film; and discharging the mixed fluids through a first fluid discharge channel connected to the second region.

The method may further include: filtering the mixed fluids by contacting the mixed fluids in the second region with a filter film dividing the region under the turbulent flow generation film into the second region and a third region; collecting the filtered fluid in the third region; and discharging the filtered fluid through a second fluid discharge channel connected to the third region.

The method may further include loading water into the first region to control the viscosity of the fluids.

According to an embodiment of the present invention, the water and the fluids may be simultaneously loaded, or the water may be loaded before the fluids are loaded.

The method may further include injecting gas to the fluids in the first region.

According to one or more embodiments of the present invention, an apparatus for mixing fluids includes: a chamber including a first region and a second region; a fluid influx channel connected to the first region through which a plurality of fluids flow into the chamber; a turbulent flow generation film interposed between the first region and the second region that includes through-holes to generate of turbulent flow in the fluids in the second region to mix the fluids; and a first fluid discharge channel connected to the second region through which the mixed fluids are discharged.

The apparatus may further include: a filter film located under the second region for filtering the mixed fluids; a third region located under the filter film for storing the filtered mixed fluids; and a second fluid discharge channel connected to the third region through which the filtered mixed fluids are discharged.

According to an embodiment of the present invention, the filter film may include through-holes for filtering the mixed fluids.

According to an embodiment of the present invention, the filter film may include an antibody attached thereto.

According to an embodiment of the present invention, the turbulent flow generation film may include at least one material selected from the group consisting of metal, metal oxide, polymer, silicon, and glass.

According to an embodiment of the present invention, the turbulent flow generation film may include at least one material selected from the group consisting of aluminum (Al), gold (Au), platinum (Pt), copper (Cu), silver (Ag), tungsten (W), tin (Sn), titanium (Ti), aluminum oxide ($Al_2O_3$), tin oxide (SnO), polydimethylsiloxane (PDMS), polymethylmethacrylate (PMMA), polycarbonate (PC), polyamide (PA), polyethylene (PE), polypropylene (PP), polyphenylene ether (PPE), polystyrene (PS), polyoxymethylene (POM), polytetrafluoroethylene (PTFE), polyvinylchloride (PVC), polyvinylidene fluoride (PVDF), polybutyleneterephthalate (PBT), and perfluoralkoxyalkane (PFA).

According to an embodiment of the present invention, the diameter of the through-holes may be in the range of about 100 nm to about 10 μm.

The apparatus may further include a gas supplier for supplying gas to the fluids.

According to an embodiment of the present invention, the gas supplier may be connected to the fluid influx channel.

According to an embodiment of the present invention, the gas supplier may be connected to the first region.

DETAILED DESCRIPTION OF EXEMPLARY EMBODIMENTS

Figure 1:
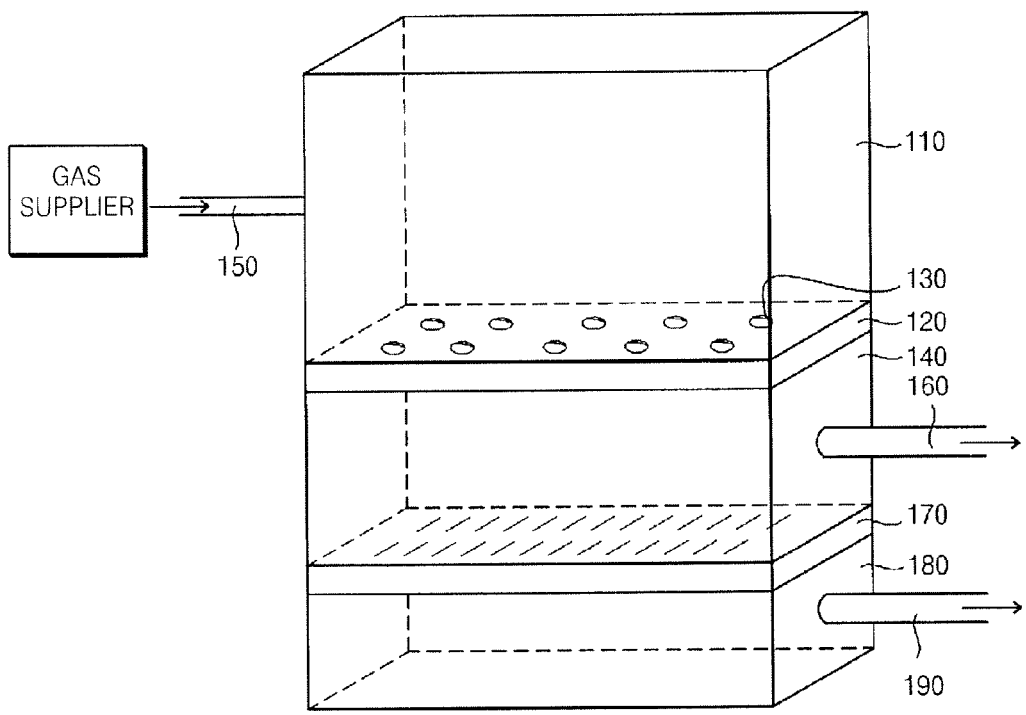
FIG. 1 is a schematic perspective view of an apparatus for mixing fluids, according to an embodiment of the invention.

Reference will now be made in detail to exemplary embodiments, examples of which are illustrated in the accompanying drawings, wherein like reference numerals refer to the like elements throughout. In this regard, the present embodiments may have different forms and should not be construed as being limited to the descriptions set forth herein. Accordingly, the embodiments are merely described below, by referring to the figures, to explain aspects of the present description.

FIG. 1 is a schematic perspective view of an apparatus for mixing fluids, according to an embodiment of the invention.

Referring to FIG. 1, the apparatus for mixing fluids according to an embodiment of the invention includes a chamber 100 including a first region 110 and a second region 140, a fluid influx channel 150 which is connected to the first region 110 of the chamber 100 and through which fluids flow into the chamber 100, a turbulent flow generation film 120 that is interposed between the first and second regions 110 and 140 of the chamber 100 having through-holes 130 by which a fluid in the second region 140 has a turbulent flow, and first and second fluid discharge channels 160 and 190 through which mixed fluids are discharged. The first fluid discharge channel 160 is connected to the second region 140 of the chamber 100, and the second fluid discharge channel 190 is connected to a third region 180 of the chamber 100.

The apparatus for mixing fluids is suitable for treating micro fluids in small amounts, such as nano-liters. However, in other cases, a smaller or greater amount of micro fluids may also be used.

The chamber 100 of the apparatus for mixing fluids may contain fluids having predetermined volumes, and includes a space from which the to-be-assayed fluids that are introduced and mixed or reacted are discharged. The chamber 100 may be hexahedral or cylindrical. In addition, although the chamber 100 illustrated in FIG. 1 has a rectangular cross-section, the cross-section of the chamber 100 may also be square, trapezoidal, or circular.

The chamber 100 may be formed using various methods and various materials. According to an embodiment of the invention, the chamber 100 may be formed of an insulating material. For example, the chamber 100 may be formed of silicon, glass, fused silicon, or plastic. However, the chamber 100 may also be formed of other materials.

The fluid influx channel 150 is connected to the first region 110 of the chamber 100. Fluids flow into the chamber 100 through the fluid influx channel 150.

The first region 110 of the chamber 100 is a region into which fluids are loaded before being mixed, and is located in an upper portion of the chamber 100. In general, micro or nano fluids have low flow rates and small Reynolds numbers and thus, fluids having different particles, when loaded into the first region 110 of the chamber 100, do not mix and easily flow in a laminar flow pattern. Thus, the first region 110 of the chamber 100 contains unmixed fluids.

According to an embodiment of the invention, an apparatus for mixing fluids may include at least one fluid influx channel 150. If the apparatus for mixing fluids includes only one fluid influx channel 150, different types of fluids may be simultaneously or sequentially loaded into the first region 110 of the chamber 100 through the fluid influx channel 150. On the other hand, if the apparatus for mixing fluids includes at least two fluid influx channels 150, different types of fluids may be loaded into the first region 110 of the chamber 100 through different fluid influx channels 150.

According to an embodiment of the invention, the fluid influx channel 150 may be connected to various sites of the first region 110 of the chamber 100. For example, the fluid influx channel 150 may be connected to a left surface, right surface, or top surface of the first region 110. If at least two fluid influx channels 150 are used, the fluid influx channels 150 may be connected to the same surface of the first region 110 or connected to different surfaces of the first region 110.

The diameter of the fluid influx channel 150 may be substantially less than the length of a sidewall of the first region 110 in which the fluid influx channel 150 is formed. When a fluid flowing in the fluid influx channel 150 enters the first region 110, some of the fluid rotates near the sidewall of the first region 110 and thus a cross current may be formed.

The turbulent flow generation film 120 is disposed between the first and second regions 110 and 140 of the chamber 100. The turbulent flow generation film 120 has the through-holes 130 by which turbulent flow of the fluids in the second region 140 is generated.

Since the turbulent flow generation film 120 has the through-holes 130, fluids flow from the first region 110 of the chamber 100 to the second region 140 of the chamber 100 through the through-holes 130 of the turbulent flow generation film 120. For example, when fluids are loaded into the first region 110 of the chamber 100 and the volume of the fluids reaches or exceeds a predetermined volume, gravity applies a predetermined pressure to the turbulent flow generation film 120, and thus, the fluids in the first region 110 flow into a lower portion of the chamber 100 through the through-holes 130 of the turbulent flow generation film 120. That is, the through-holes 130 of the turbulent flow generation film 120 act as a passage through which the fluids in the first region 110 flow into the second region 140.

When the fluids in the first region 110 flow into the second region 140 of the chamber 100 through the through-holes 130 of the turbulent flow generation film 120, turbulent flow may occur in the second region 140 of the chamber 100 and thus fluids may be mixed in the second region 140. For example, when the fluids in the first region 110 flow into the second region 140 through the through-holes 130 of the turbulent flow generation film 120, bubbles may be formed. When bubbles grow and reach a predetermined size, the bubbles burst, causing the fluids in the second region 140 to flow in a turbulent flow pattern, thereby mixing the fluids in the second region 140 corresponding to the lower portion of the chamber 100. The thickness of the turbulent flow generation film 120 may be appropriately controlled according to the size of the chamber 100. For example, the thickness of the turbulent flow generation film 120 may have a thickness of about 0.1 μm to about 1 mm.

According to an embodiment of the invention, since the turbulent flow is generated by the through-holes 130 of the turbulent flow generation film 120, a any material that can maintain the shape of the turbulent flow generation film 120 may be used for forming the turbulent flow generation film 120. For example, the material for forming the turbulent flow generation film 120 may be metal, metal oxide, a polymer, silicon, or glass. In this regard, the metal may be aluminum (Al), gold (Au), platinum (Pt), copper (Cu), silver (Ag), tungsten (W), tin (Sn), titanium (Ti), or mixtures thereof. The metal oxide may be aluminum oxide ($Al_2O_3$), tin oxide (SnO), or mixtures thereof.

The polymer may be polydimethylsiloxane (PDMS), polymethylmethacrylate (PMMA), polycarbonate (PC), polyamide (PA), polyethylene (PE), polypropylene (PP), polyphenylene ether (PPE), polystyrene (PS), polyoxymethylene (POM), polytetrafluoroethylene (PTFE), polyvinylchloride (PVC), polyvinylidene fluoride (PVDF), polybutyleneterephthalate (PBT), or perfluoralkoxyalkane (PFA). These polymers may be used alone or in combination.

According to an embodiment of the invention, the shape or arrangement of the through-holes 130 formed in the turbulent flow generation film 120 is substantially unlimited as long as the mixing of the fluids is unhindered. For example, the through-holes 130 formed in the turbulent flow generation film 120 may all have substantially the same shape, or in other cases, some of the through-holes 130 may be circular and the other through-holes 130 may be square. With respect to the arrangement of the through-holes 130, the through-holes 130 may be regularly arranged at predetermined intervals, or in other cases, may be irregularly arranged in a predetermined structure. The interval between adjacent through-holes 130 may be appropriately adjusted as long as formation of fluid-induced bubbles is not hindered. The interval between adjacent through-holes 130 may be greater than diameters of the bubbles. If the interval between adjacent through-holes 130 is less than diameters of the bubbles, formed bubbles may contact each other and burst before they grow to a predetermined size resulting in an insufficient turbulent flow in the lower portion of the chamber 100.

According to embodiments of the invention, each of the through-holes 130 may have a diameter in the range of about 100 nm to about 10 μm. If the diameters of the through-holes 130 are equal to or less than about 100 nm, a capillary pressure at the through-holes 130 increases and thus, bubbles induced from the fluids may be too small for the fluids to be sufficiently mixed under the turbulent flow generation film 120. On the other hand, if the diameters of the through-holes 130 are equal to or greater than about 10 μm, fluids in the first region 110 may pass through the through-holes 130 without forming bubbles and thus, the fluids in the second region 140 may be insufficiently mixed.

The turbulent flow generation film 120 including the through-holes 130 may be manufactured using a hot embossing process, an injection molding process, a casting process, a stereolithography process, a laser ablation process, a rapid prototyping process, or a silk screen process. In addition, the turbulent flow generation film 120 may also be manufactured using a mechanical process such as a numerical control (NC) machining process, or a semiconductor manufacturing process using deposition and etching processes.

According to an embodiment of the invention, bubbles formed when fluids pass through the through-holes 130 of the turbulent flow generation film 120 grow and upon reaching a predetermined size, burst. When the bubbles burst, a predetermined amount of force is applied to the fluids in the second region 140. Due to the force, the fluids in the second region 140 flow turbulently. Thus, the fluids in the second region 140 are mixed with each other. Since the fluids gradually flow from the first region 110 to the second region 140 through the through-holes 130 of the turbulent flow generation film 120, bubbles are continuously formed until all of the fluids in the first region 110 flow into the second region 140 and thus, the fluids are also continuously mixed in the second region 140.

As illustrated in FIG. 1, the first fluid discharge channel 160 is connected to the second region 140. The mixed fluids flow out of the second region 140 of the chamber 100 through the first fluid discharge channel 160. That is, the fluids mixed in the second region 140 flow out of the apparatus for mixing fluids through the first fluid discharge channel 160 and are provided to another apparatus.

According to an embodiment of the invention, the apparatus for mixing fluids may further include a filter film 170 that is disposed under the second region 140 and filters the mixed fluids, a third region 180 of the chamber 100 that stores the filtered fluids, and the second fluid discharge channel 190 that is connected to the third region 180 and discharges the filtered fluids.

If fluids having different properties react with each other by being mixed in the second region 140 of the chamber 100 to form a reaction product, the filter film 170 isolates the reaction product from the other material. For example, the newly formed reaction product may remain in the second region 140, and an unreacted material may pass through the filter film 170 and gather in the third region 180 of the chamber 100. Alternatively, the newly formed reaction product may move into and gather in the third region 180, and the unreacted material may remain in the second region 140. In addition, some materials can bind to the unreacted material excluding the newly formed reaction product, for example, an antibody attached to the filter film 170 so that the unreacted material attaches to the filter film 170. Meanwhile, the newly formed reaction product that is not attached to the filter film 170 is stored in the third region 180 of the chamber 100 and then flows out of the apparatus for mixing fluids through the second fluid discharge channel 190. In addition, the filter film 170 may be formed in such a pattern that only a material comprised of particles or molecules of a predetermined size is allowed to pass therethrough. In this regard, through-holes may be formed in the filter film 170 to allow only a final desired material to pass through and gather in the third region 180.

In other embodiments of the invention, if only a mixture of fluids having different properties occurs in the second region 140, the apparatus for mixing fluids may not include the filter film 170, the third region 180, and the second fluid discharge channel 190.

According to embodiments of the invention, the apparatus for mixing fluids may further include a gas supplier (not shown). Due to the gas supplier, when fluids pass through the through-holes 130 of the turbulent flow generation film 120, bubbles are more easily formed. The larger the bubbles formed by the through-holes 130 of the turbulent flow generation film 120, the greater the force applied to fluids in the second region 140 and thus the fluids may be more easily mixed. Thus, when gas is supplied to the fluids using the gas supplier, larger bubbles are formed and thus, the fluids in the second region 140 may form a more turbulent flow.

The gas supplier may be connected to the fluid influx channel 150. In addition, the gas supplier may be directly connected to the first region 110 of the chamber 100. In this case, the gas supplier and the fluid influx channel 150 may be located on the same surface or different surfaces of the first region 110 of the chamber 100. Since the gas supplier is used to form larger bubbles and thus more efficiently mix fluids, the gas supplier is optionally included in the apparatus for mixing fluids.

The apparatus for mixing fluids according to the embodiments described above may be used in a biochip such as a lab-on-a-chip, or a biosensor in which samples need to be mixed. When a biochip is used to measure the concentration of an analyte by using an optical method, a material that reacts with an analyte and causes fluorescent light emissions or color change, is used to determine the concentration of the analyte based on a change in fluorescence or light absorbance before and after use of the material. In this case, the analyte is mixed with the material that emits a fluorescent light or changes color. The apparatus for mixing fluids according to the embodiments described above may efficiently mix a small amount of fluid by using the turbulent flow generation film 120 having the through-holes 130 without additional external devices. When the apparatus for mixing fluids is applied to the biochip or the biosensor, small biochips and biosensors may be manufactured that can efficiently mix a small amount of fluid. Thus, integration and accuracy of the biochip and the biosensor may be improved.

In addition, an apparatus for mixing fluids may include a film therein to induce turbulent flow of fluids without the use of an additional external device and thus a small amount of fluid are easily mixed. That is, since additional devices for generating turbulent fluid flow are not used, the apparatus for mixing fluids according to the embodiments described above may be efficiently applied to micro devices such as a lab-on-a-chip.

Figure 2:
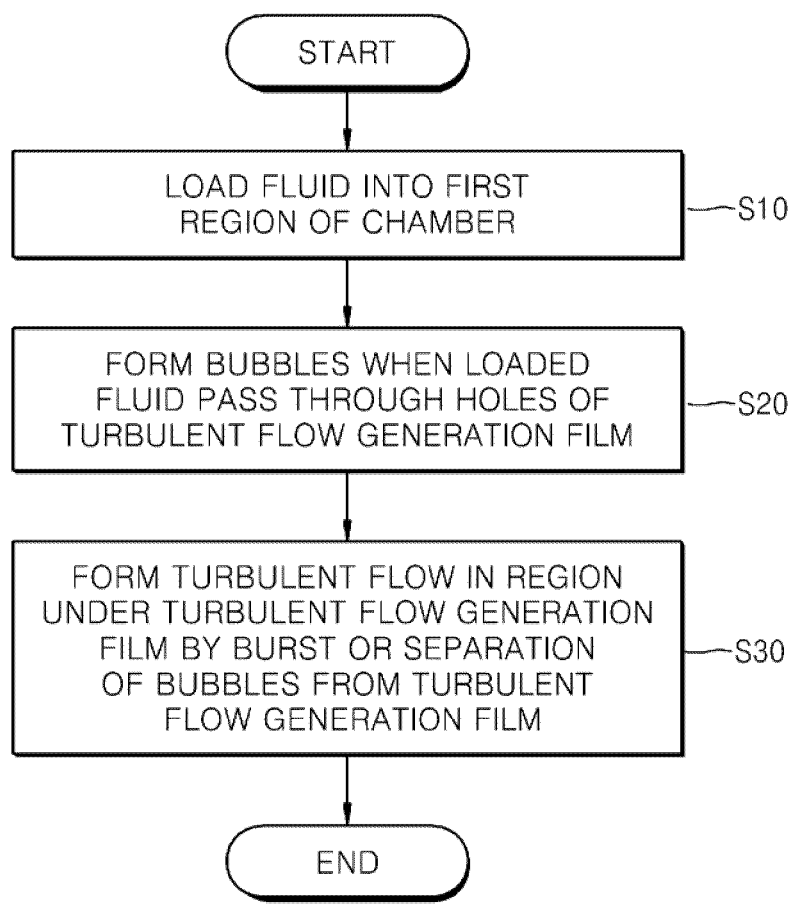
FIG. 2 is a flowchart of a method of mixing fluids, according to an embodiment of the invention.
Figure 3A:
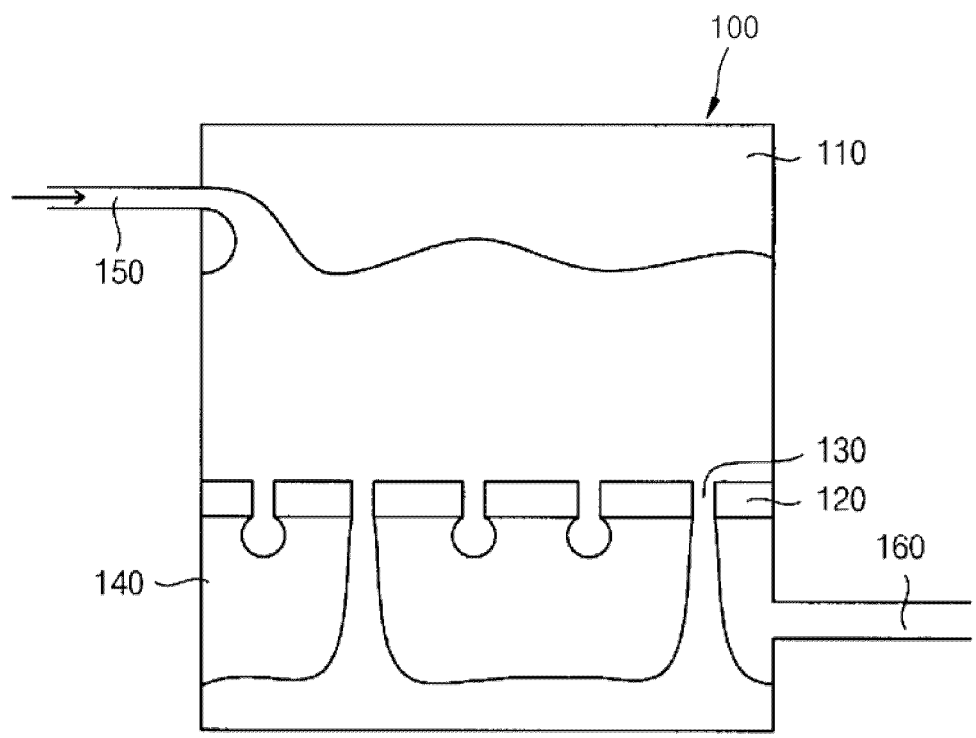
FIGS. 3A through 3C are sectional views of an apparatus for mixing fluids according to another embodiment of the invention.
Figure 3B:
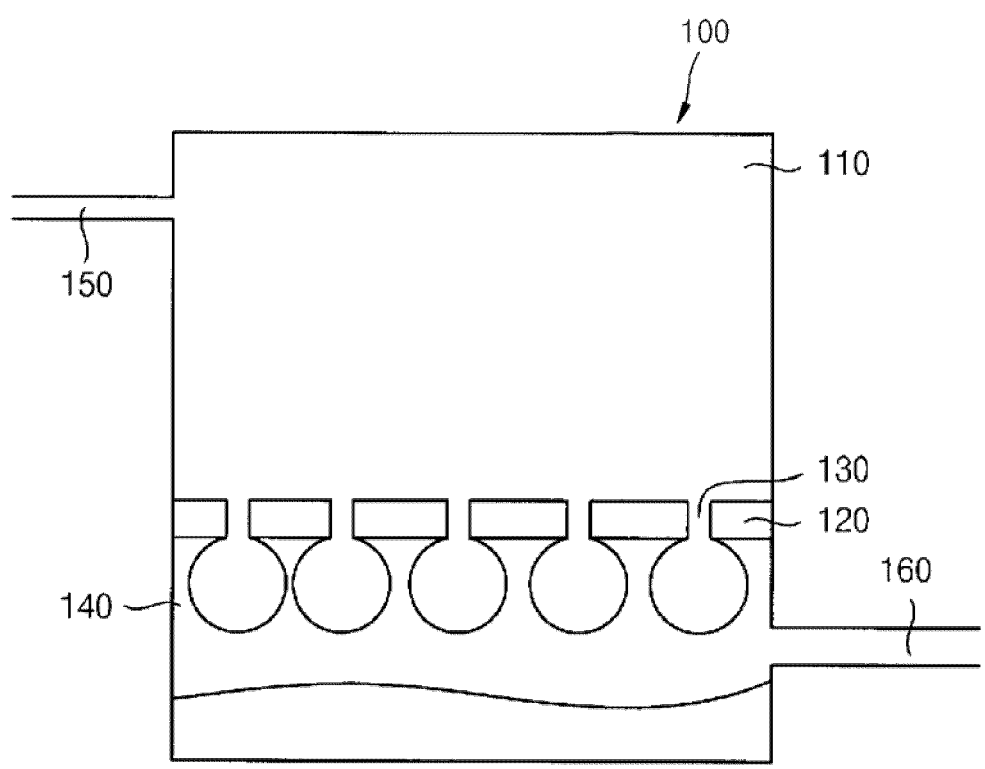
Figure 3C:
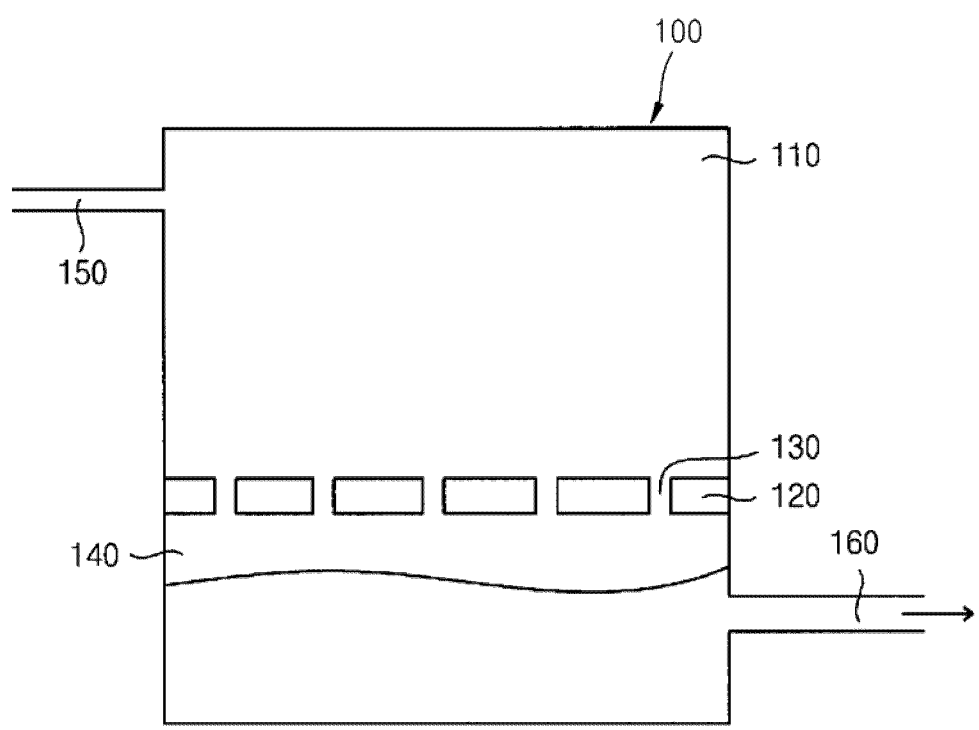

FIG. 2 is a flowchart for a method of mixing fluids, according to an embodiment of the invention, and FIGS. 3A through 3C are sectional views of an apparatus for mixing fluids according to another embodiment of the invention.

Referring to FIGS. 2 and 3A, fluids are supplied to the first region 110 of the chamber 100 through the fluid influx channel 150 (Operation S10).

A fluid analyte is supplied to the first region 110 through the fluid influx channel 150. The first region 110 is located above the turbulent flow generation film 120. The fluid analyte is not limited and may be any fluid that is to be homogeneously mixed. For example, the fluid analyte may be a bodily fluid such as blood, sweat, saliva, or urine, or a microorganism cultured solution. The fluid analyte may include an antigen, an antibody, an amino acid, DNA, RNA, or a nucleotide.

According to an embodiment of the invention, different types of fluids may be simultaneously or sequentially loaded into the same fluid influx channel 150. When different types of fluids are sequentially loaded into the same fluid influx channel 150, a fluid having lower density may be loaded first to more effectively mix the fluids. According to another embodiment of the invention, different types of fluids may be loaded through different influx channels. In this case, the different fluid influx channels may be disposed on different surfaces of the first region 110 of the chamber 100, or the same surface of the first region 110 of the chamber 100.

When fluids are loaded through the fluid influx channel 150, the loaded fluids fill the first region 110 of the chamber 100. The fluids loaded into the first region 110 may flow in a laminar flow pattern because they are micro fluids and thus have low flow rates and small Reynolds numbers.

If the amount of the fluids in the first region 110 reaches or exceeds a predetermined amount, the fluid mass applies pressure to the turbulent flow generation film 120, and the fluids flow into the second region 140 disposed under the turbulent flow generation film 120 through the through-holes 130 of the turbulent flow generation film 120. When the fluids are initially loaded, the turbulent flow generation film 120 is not wet and thus a small amount of the fluids may flow into the second region 140 through the through-holes 130 of the turbulent flow generation film 120 without formation of bubbles. However, after the turbulent flow generation film 120 contacts the fluids, the turbulent flow generation film 120 becomes wet due to the fluids. As a result, when the fluids gradually pass through the through-holes 130 of the turbulent flow generation film 120, bubbles are formed.

Referring to FIGS. 2 and 3B, when the fluids loaded into the chamber 100 pass through the through-holes 130 of the turbulent flow generation film 120 in the chamber 100, bubbles are formed (Operation S20).

Referring to FIGS. 2 and 3C, when viscous fluids pass through a narrow gap or opening, bubbles are formed due to dissolved gases in the fluids themselves or an additionally loaded gas while balancing a capillary pressure which affects fluid mixtures, a surface tension, and a fluid buoyant force. The bubbles gradually swell and when the bubble volumes reach a predetermined level, the bubbles completely separate from the turbulent flow generation film 120 and either flow into the second region 140 or burst (Operation S30). The bursting bubbles apply a predetermined force to the fluids in the second region 140 located under the turbulent flow generation film 120, thus causing turbulent flow that mixes the fluids. Thus, according to a method of mixing fluids of another embodiment of the invention, turbulent fluid flows may occur without the use of other external forces or apparatuses other than the turbulent flow generation film 120 in the chamber 100.

The method of mixing fluids according to the present embodiment of the invention may further include an operation of loading water. In general, the bubble volumes generated by the through-holes 130 are inversely proportional to the viscosity of the fluids. Thus, when the viscosity of fluids is high, the viscosity of the fluids may be lowered by mixing water with the fluids. According to an embodiment of the invention, water and the fluids may be simultaneously loaded into the chamber 100, or water may be loaded into the chamber 100 before the fluids are loaded. In general, water has lower density than the fluids. Thus, when water is loaded after the fluids are loaded, the water layer may separate from the fluids layer. Therefore, water may be loaded before the fluids are loaded, or water and the fluids may be simultaneously loaded. In addition, when water is loaded first into the chamber 100, the turbulent flow generation film 120 becomes wet due to the water. Thus, when the fluids are loaded into the first region 110 and pass through the through-holes 130, bubbles may be more easily formed.

The method of mixing fluids according to the present embodiment may further include an operation of injecting gas. By injecting the gas, the fluids passing through the through-holes 130 of the turbulent flow generation film 120 may form larger bubbles and thus, a stronger force may be applied to the fluids under the turbulent flow generation film 120. According to an embodiment of the invention, the operation of injecting gas and the operation of loading the fluids into the first region 110 above the turbulent flow generation film 120 may be simultaneously performed.

A method of mixing fluids according to an embodiment of the invention may further include an operation of filtering the mixed fluids. When materials included in the fluids react with each other due to fluid mixing to form a new material not included in the initially loaded fluids, the new material formed by the reaction may be isolated by filtering the mixed fluids. The filtering method may vary according to the type of a material used.

According to an embodiment of the invention, the filtering method may use the filter film 170 located under the turbulent flow generation film 120 having the through-holes 130 to filter the new material. For example, an antibody or enzyme which is linkable to an unreacted material in the fluids may be attached as a binder to the filter film 170. Thus, only newly formed reaction products that are not linked to the binder can pass through the filter film 170 and gather in the third region 180 under the filter film 170 of the chamber 100. Alternatively, if the unreacted material is electrically charged, for example, negatively (−) or positively (+) charged, and the newly formed reaction products are not electrically charged, electricity may be applied to the filter film 170 so that the newly formed reaction products can pass through the filter film 170 to be filtered. Alternatively, the filter film 170 may be formed in such a way that only particles having a predetermined size or less pass therethrough, to filter particles having a desired size. In addition to the methods described above, various other methods according to other embodiments of the invention may be used to filter a desired material according to the reaction products.

A method of mixing fluids according to an embodiment of the invention may further include an operation of discharging the filtered fluids. By discharging the fluids, the filtered fluids may be acquired by another apparatus.

Figure 4:
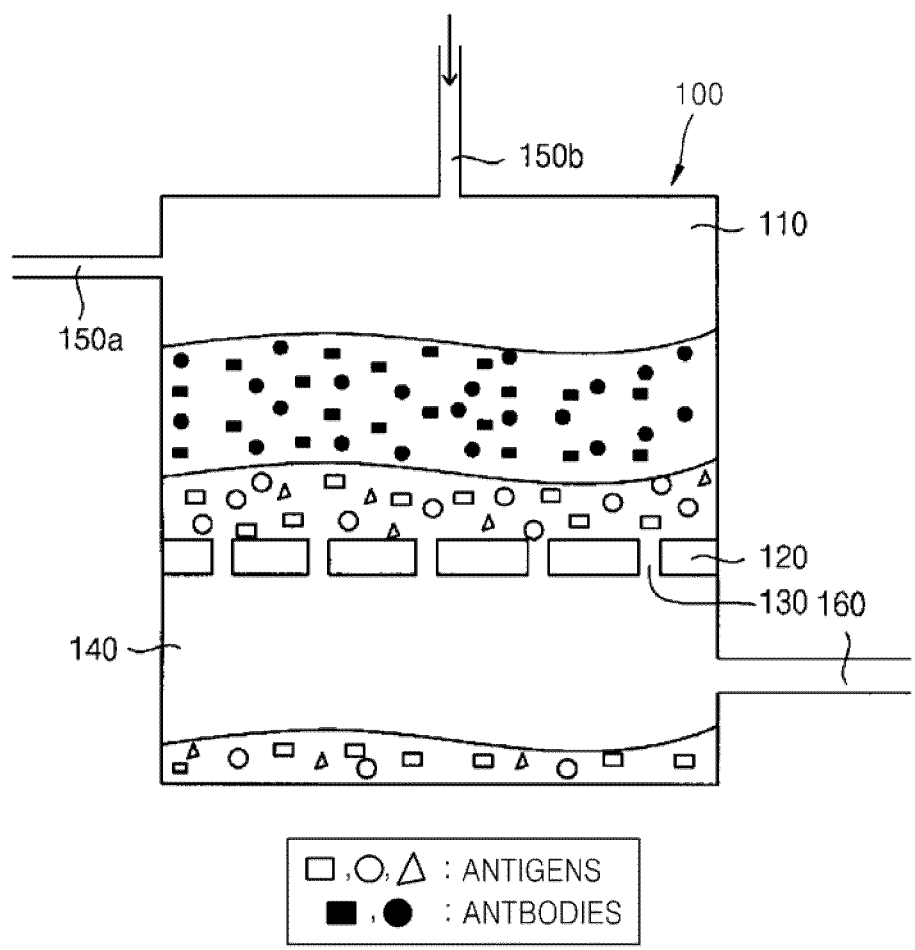
FIGS. 4 through 6 are sectional views of an apparatus for mixing fluids, according to an embodiment of the invention.
Figure 5:
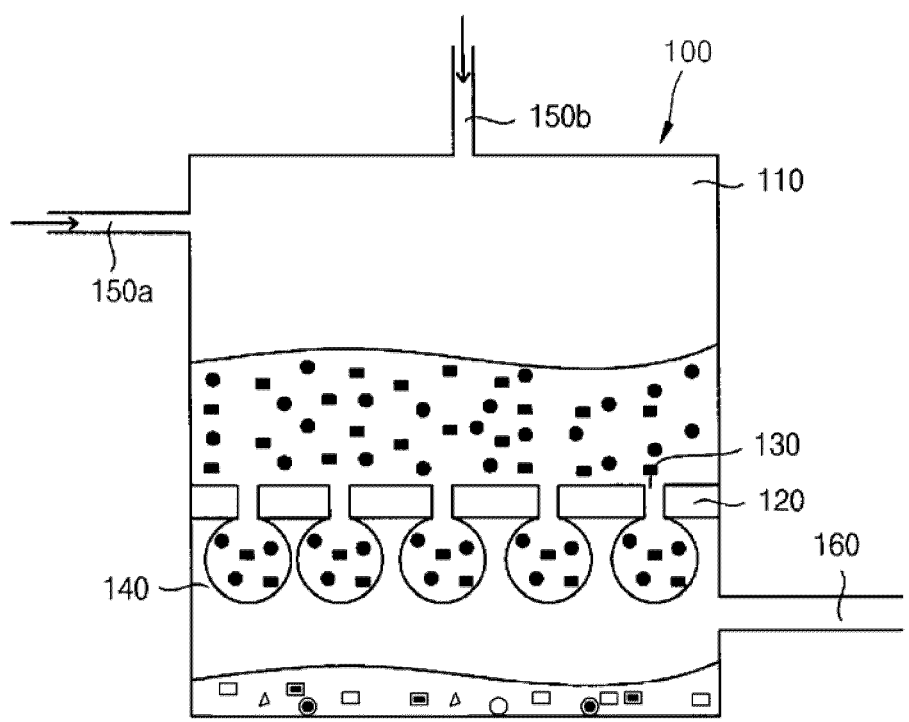
Figure 6:
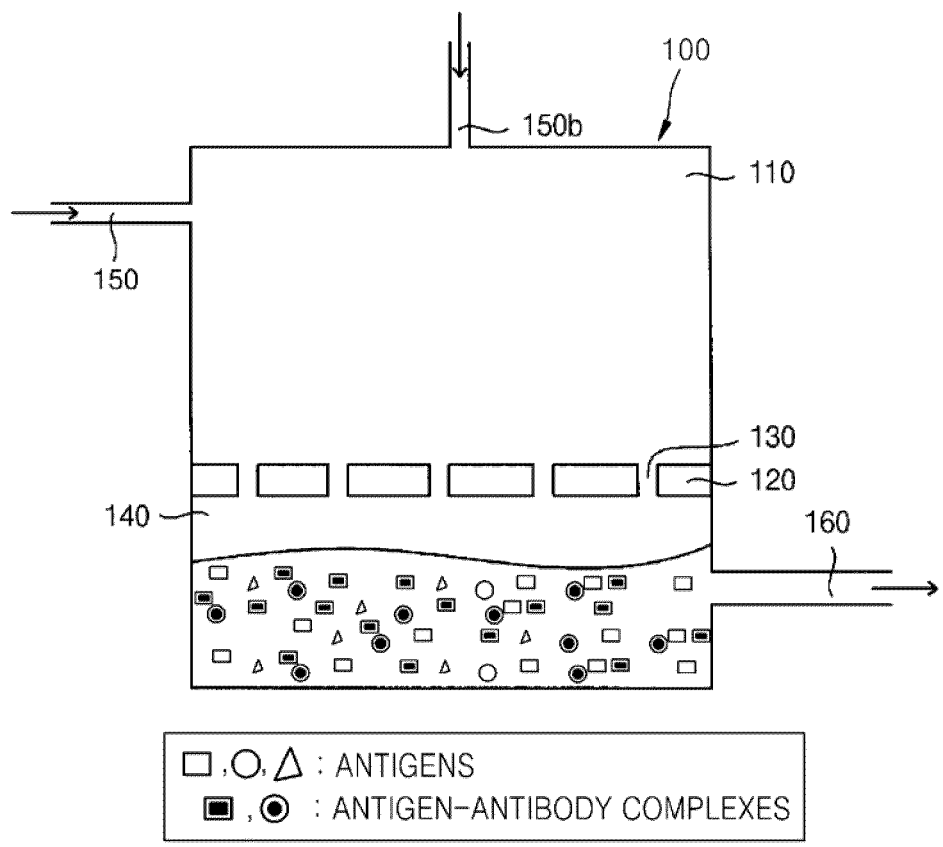

FIGS. 4 through 6 are sectional views for explaining methods of mixing fluids according to an embodiment of the invention. Although FIGS. 4 through 6 illustrate a method according to an embodiment of the invention of mixing a fluid including an antigen that includes a protein or polypeptide and a fluid including an antibody that is linkable to the antigen, it may be understood that characteristics of the disclosed method are also applicable to methods of mixing fluids including various other biomolecular materials.

Referring to FIG. 4, the first fluid is loaded into the first region 110 of the chamber 100 through a first fluid influx channel 150a. Meanwhile, the second fluid is loaded into the first region 110 of the chamber 100 through a second fluid influx channel 150b. According to embodiments of the invention, the first fluid may include various proteins or polypeptides acting as antigens, and the second fluid may include antibodies that are linkable to the antigens such as the proteins or polypeptides. For example, to identify whether the first fluid contains a material that causes an allergic reaction in a patient, the second fluid may include antibodies which are linkable to the antigens that cause an allergic reaction in the patient and to which a material that expresses fluorescence when linked is attached.

Although FIG. 4 illustrates the first and second fluids loaded through different influx channels, the first and second fluids may also be loaded into the first region 110 of the chamber 100 through only one of the first fluid influx channel 150a and the second fluid influx channel 150b.

In a case in which the first and second fluids are loaded into the first region 110, since antigens and antibodies contained in the first and second fluids may have different molecular weights, the first and second fluids may not mix and may form separate layers in the first region 110. According to the embodiment illustrated in FIG. 4, the first fluid containing the antigens is located under the second fluid containing the antibodies.

When the first and second fluids are loaded into the first region 110 of the chamber 100, initially, the turbulent flow generation film 120 may not be wetted by the first and second fluids and bubbles may not be formed. That is, the first and second fluids that are loaded into the first region 110 of the chamber 100 may initially flow into the second region 140 through the through-holes 130 without formation of bubbles.

Referring to 5, after bubbles are formed when the first and second fluids pass through the through-holes 130 of the turbulent flow generation film 120, the bubbles may either burst or separate from the turbulent flow generation film 120, thereby generating the turbulent flow in the second region 140 and thus mixing the first and second fluids.

Among the fluids loaded into the first region 110 of the chamber 100, some of the first fluid located under the second fluid flows into the second region 140 of the chamber 100 through the through-holes 130 of the turbulent flow generation film 120 and the turbulent flow generation film 120 becomes wet. Once the turbulent flow generation film 120 is wet, bubbles are formed when the first and second fluids pass through the through-holes 130 of the turbulent flow generation film 120.

When the bubbles reach a predetermined size, the bubbles burst or flow into the second region 140 of the chamber 100 so that the fluids gathered in the second region 140 flow in a turbulent flow pattern. When the turbulent flow occurs, the fluids in the second region 140 mix. When the fluids in the second region 140 are mixed, the antibodies contained in the second fluid link to the antigens contained in the first fluid, and the second region 140 fills with the antigen-antibody complexes, the antigens and the antibodies.

Referring to FIG. 6, the mixed fluids are discharged from the apparatus for mixing fluids through the first fluid discharge channel 160 connected to the second region 140 of the chamber 100.

When the fluids in the first region 110 pass through the through-holes 130 of the turbulent flow generation film 120 and flow into the second region 140, bubbles are continually formed and the fluids in the second region 140 are mixed. When the fluids in the first region 110 flow into the second region 140 and the amount of the mixed fluids in the second region 140 reaches or exceeds a predetermined amount, the fluids containing the antigen-antibody complexes, the antigens and the antibodies are discharged from the apparatus for mixing fluids through the first fluid discharge channel 160.

To measure the amount of a target antigen contained in the first fluid, the discharged mixed fluids are then subjected to an operation of measuring fluorescence. Thus, fluorescence expressed by the antigen-antibody complexes may be measured.

Figure 7:
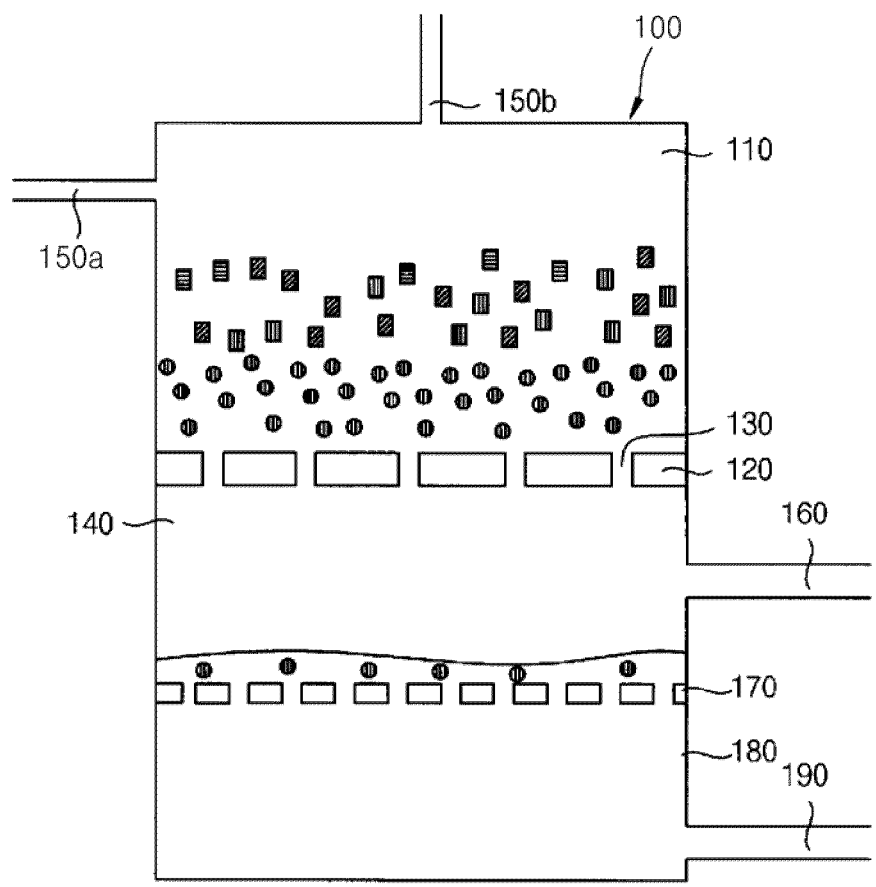
FIGS. 7 through 9 are sectional view of an apparatus for mixing fluids, according to another embodiment of the invention.
Figure 8:
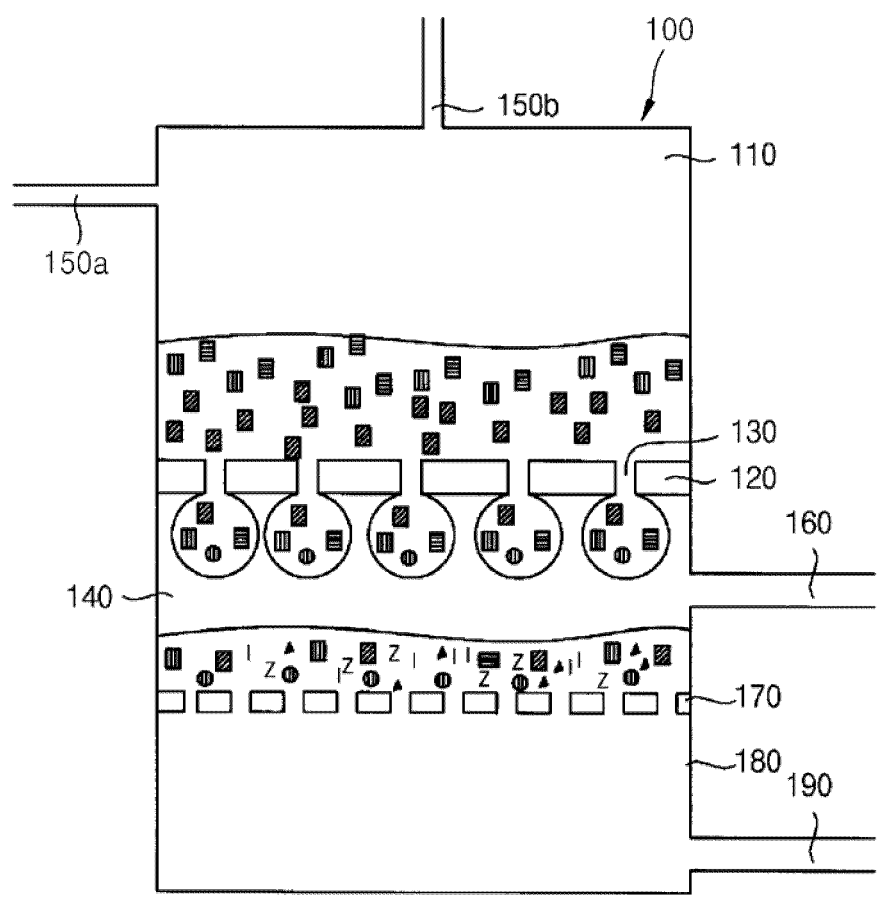
Figure 9:
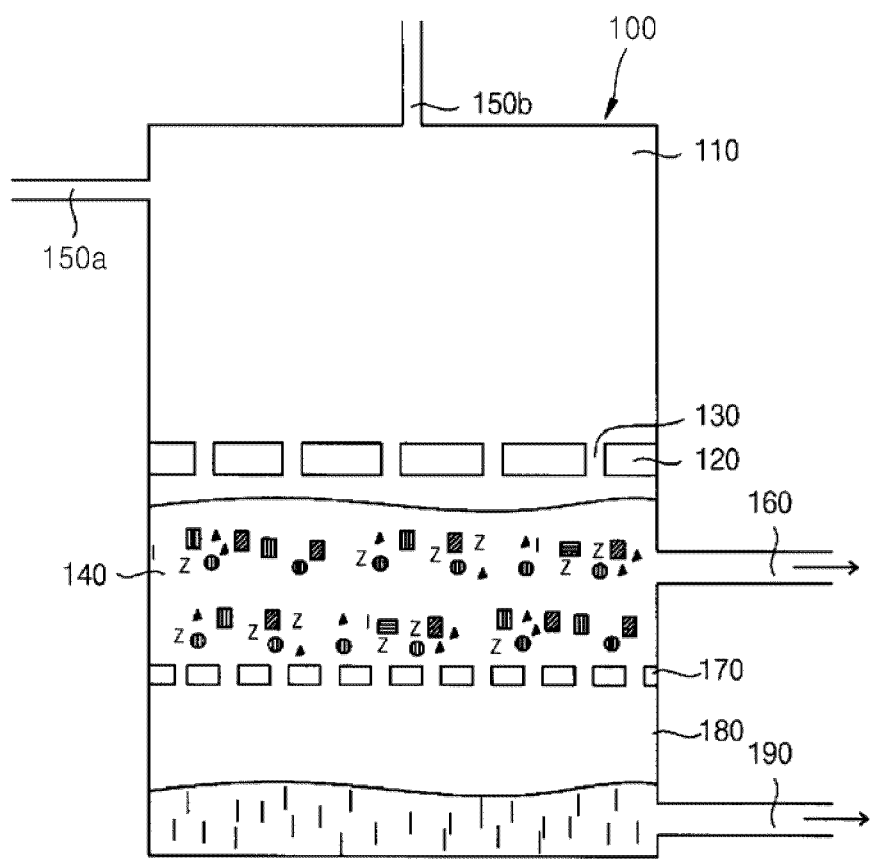

FIGS. 7 through 9 are sectional views for explaining a method of mixing fluids according to another embodiment of the invention. Although FIGS. 7 through 9 illustrate a method according to an embodiment of the invention of acquiring DNA by dissolving cells, it may be understood that characteristics of the disclosed method are also applicable to cases in which fluids to be mixed contain various other biomolecular materials.

Referring to FIG. 7, a first fluid is loaded into the first region 110 of the chamber 100 through the first fluid influx channel 150a. Meanwhile, a second fluid is loaded into the first region 110 of the chamber 100 through the second fluid influx channel 150b. According to the embodiment of the invention, the first fluid may contain cells from which DNA is to be extracted, and the second fluid may contain a chelating agent or compounds such as sodium dodecyl sulfate (SDS) for dissolving the cells and extracting DNA. Although FIG. 7 illustrates the first and second fluids loaded through different influx channels, the first and second fluids may also be loaded through only one of the first and second fluid influx channels 150a and 150b. Alternatively, the first and second fluids may be simultaneously loaded through the same fluid influx channel, or the first and second fluids may be sequentially loaded.

In a case in which the first and second fluids are loaded into the first region 110, since materials contained in the first and second fluids have different molecular weights, the first and second fluids may not mix and may form separate layers in the first region 110. According to the embodiment illustrated in FIG. 7, the first fluid is located under the second fluid.

When the first and second fluids are loaded into the first region 110 of the chamber 100, initially, the turbulent flow generation film 120 may not be wetted by the first and second fluids and bubbles may not be formed. That is, the first and second fluids that are loaded into the first region 110 of the chamber 100 may initially flow into the second region 140 through the through-holes 130 without formation of bubbles.

Referring to 8, after bubbles are formed when the first and second fluids pass through the through-holes 130 of the turbulent flow generation film 120, the bubbles may either burst or separate from the turbulent flow generation film 120, thereby generating the turbulent flow in the second region 140 and thus mixing the first and second fluids.

Among the fluids loaded into the first region 110 of the chamber 100, some of the first fluid located under the second fluid flows into the second region 140 of the chamber 100 through the through-holes 130 of the turbulent flow generation film 120 and the turbulent flow generation film 120 becomes wet. Once the turbulent flow generation film 120 is wet, bubbles are formed when the first and second fluids pass through the through-holes 130 of the turbulent flow generation film 120.

When the bubbles reach a predetermined size, the bubbles burst or flow into the second region 140 of the chamber 100 so that the fluids gathered in the second region 140 flow in a turbulent flow pattern. When turbulent flow occurs, the fluids in the second region 140 mix. When the fluids in the second region 140 mix, the cells contained in the second fluid may contact the materials for dissolving the cells and thus, cell membranes of the cells and membranes of cell organelles collapse and DNA-containing intracellular materials are released from the cells. Thus, the second region 140 contains the mixed fluids including undissolved cells, the materials for dissolving the cells, DNA of the cells, and the intracellular materials. Referring to FIG. 9, the mixed fluids in the second region 140 are filtered by the filter film 170 and the filtered fluids gather in the third region 180. Then, the filtered fluids are discharged from the apparatus for mixing fluids through the second fluid discharge channel 190.

The second region 140 of the chamber 100 may include, in addition to a desired material, various other materials that are generated when the cells are dissolved. To isolate the DNA from these materials, the mixed fluids in the second region 140 are filtered.

According to embodiments of the invention, the filter film 170 may have through-holes that allow only a material having particles or molecules of a desired size to pass therethrough. For example, through-holes that allow only DNA released by dissolving the cells to pass therethrough are formed in the filter film 170 so that the DNA is collected in the third region 180. Alternatively, antibodies that are linkable to proteins or polypeptides that are released by dissolving the cells are attached to the filter film 170 and through holes are formed in the filter film 170 so that the DNA that is not attached to the filter film 170 in the second region 140 is collected in the third region 180.

The final material collected in the third region 180 of the chamber 100 may be discharged through the second fluid discharge channel 190. According to an embodiment of the invention, after the DNA acquired in the third region 180 is discharged through the second fluid discharge channel 190, an electrophoresis operation may be performed on the DNA to assay the DNA.

As described above, in the methods of mixing fluids according to embodiments of the invention, since bubbles are formed by passing fluids through through-holes formed in a film, a turbulent flow may occur in a region under the film. Due to the formation of the turbulent flow, small amounts of fluids may be efficiently mixed. In addition, since, except for the film having the through-holes, additional external forces or devices are not used, methods according to embodiments of the invention may be used in fluid control devices.

It should be understood that the exemplary embodiments described therein should be considered in a descriptive sense only and not for purposes of limitation. Descriptions of features or aspects within each embodiment should typically be considered as available for other similar features or aspects in other embodiments.

What is claimed is:

1. An apparatus for mixing liquids, the apparatus comprising:
   a chamber comprising a first region and a second region;
   a fluid influx channel connected to the first region and through which a plurality of liquids flow into the chamber;
   a turbulent flow generation film interposed between the first region and the second region that comprises through-holes configured to generate turbulent flow and form bubbles in the liquids in the second region such that mixes the liquids are mixed when the liquids pass through the through-holes; and
   a first fluid discharge channel that is connected to the second region and through which the mixed liquids are discharged,
   wherein the diameter of the through-holes is in the range of about 100 nm to about 10 µm.

2. The apparatus of claim 1, further comprising:
   a filter film located under the second region for filtering the mixed liquids; a third region located under the filter film for storing the filtered mixed liquids; and
   a second fluid discharge channel connected to the third region through which the filtered mixed liquids are discharged.

3. The apparatus of claim 2, wherein the filter film comprises through-holes for filtering the mixed liquids.

4. The apparatus of claim 2, wherein the filter film comprises an antibody attached thereto.

5. The apparatus of claim 1, wherein the turbulent flow generation film comprises at least one material selected from the group consisting of metal, metal oxide, polymer, silicon, and glass.

6. The apparatus of claim 1, wherein the turbulent flow generation film comprises at least one material selected from the group consisting of aluminum (Al), gold (Au), platinum (Pt), copper (Cu), silver (Ag), tungsten (W), tin (Sn), titanium (Ti), aluminum oxide (Al2O3), tin oxide (SnO), polydimethylsiloxane (PDMS), polymethyhnethacrylate (PMMA), polycarbonate (PC), polyamide (PA), polyethylene (PE), polypropylene (PP), polyphenylene ether (PPE), polystyrene (PS), polyoxymethylene (POM), polytetrafluoroethylene (PTFE), polyvinylchloride (PVC), polyvinylidene fluoride (PVDF), polybutyleneterephthalate (PBT), and perfluoralkoxyalkane (PFA).

7. The apparatus of claim 1, further comprising a gas supplier for supplying gas to the liquids.

8. The apparatus of claim 7, wherein the gas supplier is connected to the fluid influx channel.

9. The apparatus of claim 7, wherein the gas supplier is connected to the first region.

10. An apparatus for mixing liquids, the apparatus comprising:
    a chamber comprising a first region for receiving a plurality of liquids, and a second region;
    a turbulent flow generation film interposed between the first region and the second region that comprises through-holes configured to generate turbulent flow and form bubbles in fluids passing from the first region to the second region so that the liquids are mixed when the liquids pass through-holes;
    a filter film located under the second region for filtering the mixed liquids; and
    a third region located under the filter film for storing the filtered mixed liquids, wherein the diameter of the through-holes is in the range of about 100 nm to about 10 µm.

11. The apparatus of claim 10, further comprising:
    a fluid influx channel connected to the first region through which said plurality of liquids flow into the chamber;
    a first fluid discharge channel connected to the second region through which the mixed liquids are discharged; and
    a second fluid discharge channel connected to the third region through which the filtered mixed liquids are discharged.

* * * * *